US00PP26504P3

(12) United States Plant Patent
Westphal

(10) Patent No.: US PP26,504 P3
(45) Date of Patent: Mar. 15, 2016

(54) *CLEMATIS* PLANT NAMED 'MISTY'

(50) Latin Name: *Clematis lanuginosa*
Varietal Denomination: Misty

(71) Applicant: Friedrich Manfred Westphal, Prisdorf (DE)

(72) Inventor: Friedrich Manfred Westphal, Prisdorf (DE)

( * ) Notice: Subject to any disclaimer, the term of this patent is extended or adjusted under 35 U.S.C. 154(b) by 104 days.

(21) Appl. No.: 14/120,184

(22) Filed: May 1, 2014

(65) Prior Publication Data

US 2015/0319895 P1 Nov. 5, 2015

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — Susan McCormick Ewoldt

(57) ABSTRACT

A new and distinct *Clematis* cultivar named 'Misty' is disclosed, characterized by short, very compact plant growth and a long flowering period. Flowers are distinctively light Violet-Blue in color. The new cultivar is a *Clematis*, suitable for ornamental garden purposes.

1 Drawing Sheet

Latin name of the genus and species: *Clematis lanuginosa.*
Variety denomination: 'MISTY'.

BACKGROUND OF THE INVENTION

The new cultivar is a product of a planned breeding program conducted by the inventor during 2008. June of 2008, the inventor, Friedrich Manfred Westphal, a citizen of Germany, made a crossing of the seed parent *Clematis lanuginosa* 'Carnaby', unpatented, with the pollen parent, *Clematis lanuginosa* 'William Kennett', unpatented Seeds originating from this crossing were planted out, and the new variety was selected Jul. 1, 2009. All work was conducted at a commercial nursery in Prisdorf, Germany.

The inventor first propagated 'Misty' by vegetative cuttings at the commercial nursery in Prisdorf, Germany in May of 2011. Subsequent generations have shown that the unique features of this cultivar are stable and reproduced true to type.

SUMMARY OF THE INVENTION

The cultivar 'Misty' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Misty' These characteristics in combination distinguish 'Misty' as a new and distinct *Clematis* cultivar:

1. Very short, compact plant habit.
2. Long flowering period
3. Distinctive very light violet blue color.
4. Large flower size

COMPARISON TO PARENT VARIETY

Plants of the new cultivar 'Misty' are similar to plants of the seed parent; *Clematis lanuginosa* 'Carnaby' in most horticultural characteristics, however, plants of the new cultivar 'Misty' are shorter and more compact. Additionally, plants of 'Misty' produce flowers that are light violet blue, whereas flowers of 'Carnaby' are pink and dark pink.

Plants of the new cultivar 'Misty' are similar to plants of the pollen parent; *Clematis lanuginosa* 'William Kennett' in most horticultural characteristics, however, plants of the new cultivar 'Misty' are shorter and more compact. Additionally, plants of 'Misty' produce flowers that are much lighter colored than the pollen parent.

COMMERCIAL COMPARISON

'Misty' can be compared to the well known, unpatented commercial variety 'Lasurster'. While 'Misty' and 'Lasurstern' are similar in most horticultural characteristics, plants of 'Misty' shorter, and produce a much lighter colored flower.

'Misty' can also be compared to *Clematis* 'Asagasumi', unpatented The varieties are similar in most horticultural characteristics, however, plants of 'Misty' are shorter, and less vigorous. Additionally, plants of 'Misty' produce flowers that are light violet blue, whereas flowers of 'Asagasumi' are white.

BRIEF DESCRIPTION OF THE PHOTOGRAPH

The accompanying photograph in FIG. 1 illustrates in full color a close up of typical foliage and flowers of 'Misty' grown outdoors in Germany. The plant is approximately 1 year old, and is planted in the ground.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Misty' plants grown in a greenhouse in Prijsdorf, Germany. Plants are approximately 1 year old, in a 1 liter nursery container. The greenhouse is unheated and unshaded. Temperatures ranged from 2° C. to 20° C. at night to 5° C. to 35° C. during the day. Measurements and numerical values represent averages of typical plant types.

Botanical classification: *Clematis lanuginosa* 'Misty'.

PROPAGATION

Time to rooting:

*Initiation*.—Approximately 30 days in the Summer at approximately 24° C.

*Rooted cuttings production*.—Approximately 65 days in the Summer at approximately 20° C. to 26° C.

Root description: Fine, fibrous.

PLANT

Growth habit: Climbing vine.

Height: Approximately 150 cm, measured from the soil line of the pot after approximately 1 year.

Plant spread: Approximately 45 cm after approximately 1 year.

Growth rate: During active growing season in Spring, approximately 20 to 30 cm per month.

Branching characteristics: One main stem, and 1 to 5 lateral branches, typically given a pinch.

Length of main stem: Approximately 120 cm.

Diameter of main stem: Approximately 0.3 cm.

Main stem color: Near RHS Yellow-Green 147A, flushed Greyed-Red 178A.

Main stem texture: Slightly pubescent.

Internode length: Varies from 7 to 9 cm.

Strength: Strong, flexible, semi-woody.

FOLIAGE

Leaf:

*Type*.—Simple.

*Arrangement*.—Opposite.

*Leaves per lateral branch*.—Average 3.

*Average length*.—Approximately 3 to 5 cm.

*Average width*.—Approximately 2.5 to 3.5 cm.

*Shape of blade*.—Narrow heart shaped.

*Apex*.—Acute.

*Base*.—Cordate.

*Margin*.—Entire.

*Texture of top surface*.—Smooth.

*Texture of bottom surface*.—Smooth.

*Leaf internode length*.—Approximately 2 cm.

*Color*.—Young foliage upper side: Near RHS Green 137C. Young foliage under side: Near RHS Green 137B. Mature foliage upper side: Near RHS Green 137A, flushed with Greyed-Red 178A. Mature foliage under side: Near RHS Green 137.

*Venation*.—Type: Pinnate. Venation color upper side: Near RHS Yellow-Green 147A, flushed Greyed-Red 178A. Venation color under side: Near RHS Green 137A, flushed Greyed-Red 178A.

*Petiole*.—Average Length: Approximately 5 to 6 cm. Color: Near RHS Greyed-Red 180A. Diameter: Approximately 0.2 cm. Texture: Smooth.

FLOWER

Bloom period:

*Natural season*.—Continuously from Spring to mid Summer.

Inflorescence type and habit: Single, axillary; flowers facing outward.

Flower longevity on plant: Approximately 14 days, after fully opened. Self-cleaning.

Quantity of flowers: Approximately 20 flowers occur over 70 days. Approximately 1 to 5 per flowering stem.

Inflorescence size:

*Diameter*.—Approximately 14 to 16 cm.

*Depth*.—Approximately 2.5 cm.

Corolla:

*Tepal arrangement*.—Single whorl, slightly overlapping.

*Quantity*.—Approximately 6 flower.

*Size*.—Length: Approximately 6 to 7 cm. Width: Approximately 2.5 cm.

*Margin*.—Entire, slightly undulating.

*Apex*.—Acute.

*Base*.—Truncate.

*Texture*.—Smooth, velvety.

Color:

*Tepals*.—When opening: Upper surface: Near RHS Violet-Blue 97A, center near 97D. Lower surface: Near RHS Violet-Blue 97B. Fully opened: Upper surface: Near RHS Violet-Blue 97B, center near 97D. Lower surface: Near RHS Violet-Blue 97C. Ageing: Upper Surface: Near RHS Violet-Blue 97C, center near 97D. Lower Surface: Near RHS Violet-Blue 97C.

Bud:

*Shape*.—Ovate.

*Length*.—Approximately 2 to 4 cm.

*Diameter*.—Approximately 1.5 cm.

*Color*.—Mainly Near RHS Violet-Blue 97D with base flushed Violet-Blue 97A.

Pedicels:

*Length*.—Approximately 4 to 8 cm.

*Width*.—Approximately 0.4 cm.

*Angle*.—Average 70°.

*Strength*.—Strong, flexible.

*Color*.—Near RHS Violet-Blue 97A.

Fragrance: None.

REPRODUCTIVE ORGANS

Stamens:

*Number*.—Approximately 80 to 100 per flower.

*Anther length*.—0.8 cm 1.2 cm.

*Anther color*.—Near RHS Purple N79A.

*Anther shape*.—Oblong.

*Pollen quantity*.—Not observed to date.

*Filament length*.—Approximately 1.2 to 2.0 cm.

*Filament aspect*.—Straight.

*Filament color*.—Near RHS Violet-Blue 97D.

Pistil:

*Number*.—Approximately 50 to 60 per flower.

*Length*.—Approximately 0.8 cm.

*Style color*.—Near RHS White 155B.

*Style length*.—Approximately 0.7 cm.

*Stigma*.—Shape: Linear. Color: Near RHS White 155B.

OTHER CHARACTERISTICS

Seeds and fruits: Not observed to date.

Disease/pest resistance: Neither resistance nor susceptibility to pathogens and pests common to *Clematis* have been observed.

Temperature tolerance: Tolerates temperatures from approximately −20° C. to 45° C.

What is claimed is:

1. A new and distinct cultivar of *Clematis* plant named 'Misty' as herein illustrated and described.

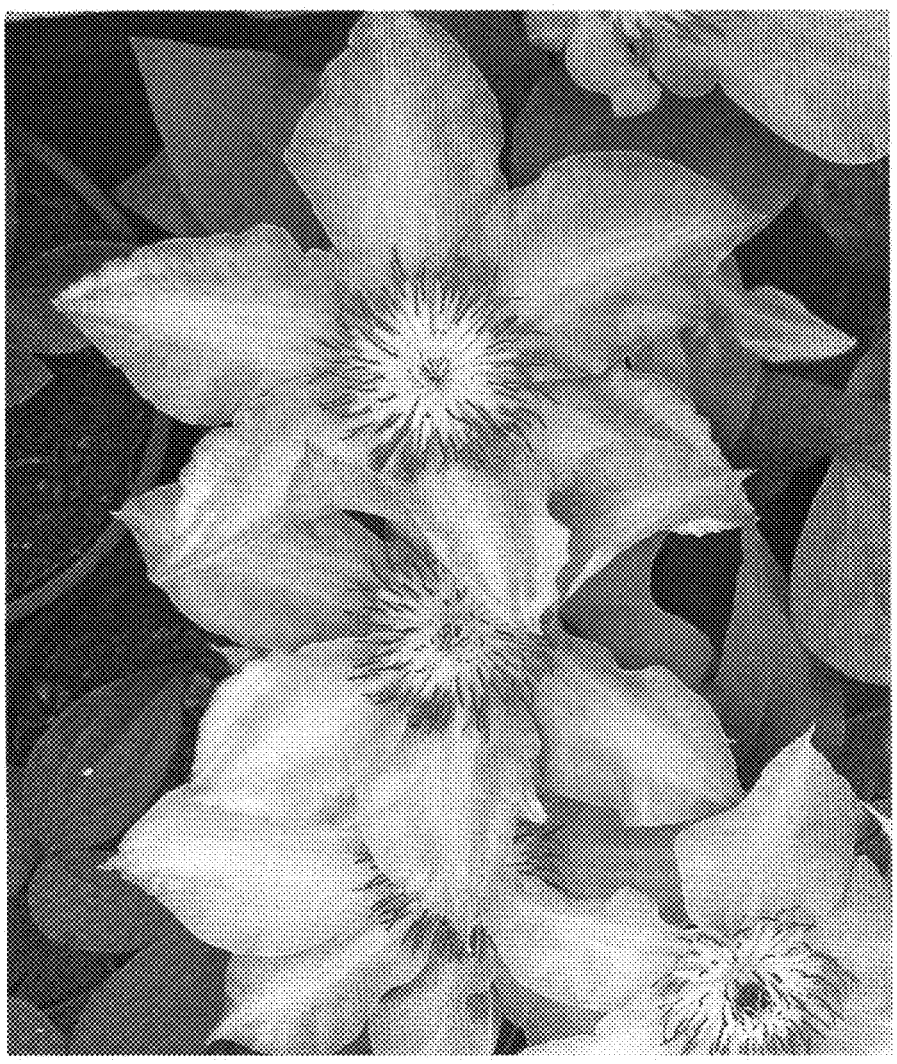

* * * * *